(12) United States Patent
Gatfield et al.

(10) Patent No.: US 6,706,500 B2
(45) Date of Patent: Mar. 16, 2004

(54) PROCESS FOR THE PREPARATION OF L-MENTHOL

(75) Inventors: Ian-Lucas Gatfield, Höxter (DE); Jens-Michael Hilmer, Höxter (DE); Uwe Bornscheuer, Greifswald (DE); Rolf Schmidt, Stuttgart (DE); Sandra Vorlová, Stuttgart (DE)

(73) Assignee: Symrise GmbH & Co. KG (DE)

( * ) Notice: Subject to any disclaimer, the term of this patent is extended or adjusted under 35 U.S.C. 154(b) by 51 days.

(21) Appl. No.: 10/041,892

(22) Filed: Jan. 7, 2002

(65) Prior Publication Data

US 2002/0182674 A1 Dec. 5, 2002

(30) Foreign Application Priority Data

Jan. 11, 2001 (DE) .......................................... 101 00 913

(51) Int. Cl.$^7$ ............................. C12P 7/00; C12P 7/02; C12N 9/20; C12N 1/00; C07H 21/04

(52) U.S. Cl. ...................... 435/132; 435/155; 435/198; 435/921; 536/23.2

(58) Field of Search ................................ 435/132, 155, 435/198, 921; 536/23.2

(56) References Cited

FOREIGN PATENT DOCUMENTS

WO      WO 99/14338    *   3/1999

OTHER PUBLICATIONS

Syldatk et al. Dechema Biotechnology Conferences, Dechema, Annual Meeting of Biotechnologists (May 30–31, 1989), Frankfurt, F.R.G.*

Langrand et al. Tetrahedron Letters 27(1) : 29–32 (1986).*

* cited by examiner

Primary Examiner—Tekchand Saidha
(74) Attorney, Agent, or Firm—Pendorf & Cutliff

(57) ABSTRACT

L-Menthol is prepared from D,L-menthyl derivatives by enantioselective enzymatic cleavage.

8 Claims, No Drawings

PROCESS FOR THE PREPARATION OF L-MENTHOL

FIELD OF THE INVENTION

The invention relates to a process for the preparation of L-menthol by enantioselective enzymatic cleavage of D,L-menthyl derivatives.

BACKGROUND OF THE INVENTION

Process for the synthetic preparation of menthol are generally known (Common Fragrance and Flavor Materials; Bauer, K., Garbe, D. and Surburg, H., Verlag V C H, Weinheim, 1990, $2^{nd}$ edition, pp. 44–46). If the products obtained are racemic mixtures, they are markedly inferior in taste and odor to the naturally occurring L-menthol, for example from peppermint oil. Therefore, there is a great interest in separation processes for D,L-menthol.

The separation can be achieved, for example, using physical processes. Such processes include, for example, fractional crystallization of the salts of optically active amines with racemic methyl hydrogen phthalate or methyl hydrogen succinate. In addition, D- or L-menthol can be separated off from racemic menthol mixtures by esterifying the mixture with an optically active acid, for example menthoxyacetic acid, and separating the mixture of diastereomeric compounds by crystallization. The D- or L-menthol is obtained by saponification of the diastereomeric ester.

A further process used industrially (DE-A 2 109 456) for separating off optically pure D- and L-menthol from D,L-menthol mixtures proceeds via a carboxylic menthyl ester as intermediate. Preferably, the esters of benzoic acid or of hexahydrobenzoic acid, and in addition the esters of 4-methylbenzoic acid, of 3,5-dinitrobenzoic acid and of 4-ethoxybenzoic acid are used. The process is the selective crystallization of optical antipodes which are obtained in a purity so high that further processing can be carried out without further purification operations.

In addition, L-menthol can be isolated from D,L-menthol mixtures using enzymes or microorganisms.

It is also known that lipases hydrolyze esters in aqueous media and can have a high specificity and selectivity. In addition, in certain organic solvents, some lipases have the ability to catalyze the back-reaction, to synthesize esters from the corresponding acids and alcohols.

Various strategies have been employed to produce pure L-menthol from the racemic D,L-menthol mixture. Thus, for example, Tetrahedron Letters, 27, (1986) 29 discloses that the lipase of *Candida cylindrarea* preferentially releases L-menthol (ee: 70%) from a racemic menthyl laurate by hydrolysis in an aqueous medium. This enantioselective preference was also displayed in the esterification of racemic menthol with lauric acid, the L-menthyl laurate being formed with high enantiomeric purity (ee: 86%). In a non-aqueous medium, racemic menthol can be enantioselectively esterified with lauric acid using lipase, with, again, the L-menthyl laurate being formed preferentially (ee: 95%). This reaction is virtually complete after 10 hours. Transesterification of D,L-menthol with trilaurin or D,L-menthyl laurate with isobutanol proceeds with a similarly high enantioselectivity, but is extremely slow (reaction time: 15 days or more).

It is also known to carry out reactions under enzyme catalysis in nonaqueous media, if the substances are only poorly soluble in water. As an alternative to organic solvents, supercritical fluids, specifically supercritical carbon dioxide, may be used. Thus, this is also disclosed for racemate resolution of D,L-menthol by Chemie Ingenieur Technik, 69, (1986) 29, more precisely by the enantioselective transesterification of various acetates with racemic menthol. The best results are achieved with the enol ester isopropenyl acetate. Such esters have the benefit that after reaction is complete, the alcohol formed by the hydrolysis, in this case isopropenyl alcohol, immediately isomerizes to form the corresponding ketone and is therefore not available for any back-reaction. The enzymes studied are lipase AY from *Candida rugosa*, lipase PS from *Burkholderia cepacia* (formerly *Pseudomonas cepacia*), Novozyme 435 from *Candida antarctica* B, lipozyme IM 60 from *Rhizomucor miehei* and esterase EP 10 from *Pseudomonas marginata*.

Esterase EP 10 can be obtained from recombinant *E. coli* strains which contain the gene for EP 10 esterase. Esterase EP 10 shows by far the highest enantioselectivities in the system. Novozyme 435, under the conditions selected, shows virtually no conversion in the transesterification using the various acetates.

The enantioselectivity of the lipase from *Candida rugosa* (lipase AY) towards racemic menthol may be significantly increased, according to the reports in Biotechnol. Prog. 11, (1995) 270 by targeted treatment of the lipase with nonionic surfactants. These studies clearly show that the effectivity of esterification of L-menthol with lauric acid in organic medium depends greatly on the enzyme. The lipase from *Candida rugosa* is significantly more effective in this reaction than the lipase from Rhizopus sp., *Burkholderia cepacia*, Pseudomonas sp., *Mucor javanicus, Aspergillus niger* and from pig pancreas. In addition, it is found that as a result of the treatment with nonionic surfactants, the effectivity of the lipase from *Candida rugosa* increases to about five fold.

Tetrahedron Letters 39, (1998) 4333 discloses that using microwave irradiation, in the case of pig pancreas lipase, leads to no change in reaction velocity or enantioselectivity in the esterification of racemic menthol with palmitic acid.

Lipases are also able to accept carboxylic anhydrides as acyl donor. Carboxylic anhydrides, as has already been mentioned in the case of the enol esters, have the advantage that acyl transfer is quasi-irreversible. According to Enzyme and Microbial Technology 18, (1996) 536, the lipase AY-30 from *Candida rugosa* is able to exercise a certain enantioselectivity in the reaction of racemic menthol with acetic anhydride, propionic anhydride and butyric anhydride. The best results with this enzyme are achieved with butyric anhydride after 48 hours in n-hexane as solvent (ee: 86% of the L-menthyl butyrate formed).

The enantioselectivity of the reaction is greatly dependent both on the lipase used and on the anhydride used. Thus, Microbiol. Biotechnol 43, (1995) 639, discloses that the lipase OF 360 from *Candida rugosa* and propionic anhydride gives a very high optical purity of the L-menthyl propionate formed (ee: 95%).

A further possible method of preparing L-menthol from D,L-menthol mixtures is to cleave racemic ester mixtures enantioselectively enzymatically. Thus, Dechema Biotechnol. Conf. (1989) 141 discloses reacting D,L-menthyl acetate with the lipase from *Candida rugosa* in a hydrolysis, the L-menthol released indicating a rather low enantioselectivity of the enzyme.

SUMMARY OF THE INVENTION

It is an object of the present invention to resolve a D,L-menthol suitable for industrial use, or derivatives thereof, with high absolute enantioselectivity, in order to obtain pure L-menthol or D-menthol or a pure L-menthyl ester or D-menthyl ester.

A process has been found for the preparation of D- or L-menthol and derivatives, characterized in that D,L-menthyl derivatives are enantioselectively enzymatically cleaved by lipases.

DETAILED DESCRIPTION OF THE INVENTION

According to the inventive process, the enantiomers are surprisingly obtained at an enantiomeric excess (ee value) of greater than 99%, and a selectivity (E value) of >100.

D,L-Menthyl derivatives for the inventive process are, for example, compounds of the formula

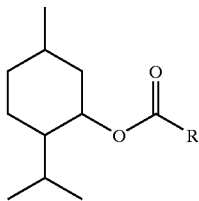

where

R denotes hydrogen, unbranched or branched $C_1$–$C_{20}$-alkyl, $C_3$–$C_8$-cycloalkyl, $C_6$–$C_{14}$-aryl, $C_7$–$C_{15}$-arylalkyl, $C_1$–$C_{20}$-alkoxy, $C_1$–$C_{20}$-alkylamino, where the above-mentioned hydrocarbon radicals can optionally be monosubstituted or polysubstituted with hydroxyl, formyl, oxy, $C_1$–$C_6$-alkoxy, carboxyl, mercapto, sulfo, amino, $C_1$–$C_6$-alkylamino or nitro or halogen, preferably chlorine.

Preferred D,L-menthyl derivatives are esters of D,L-menthol with aliphatic or aromatic carboxylic acids. For example, the following esters may be mentioned:

D,L-menthyl acetate, D,L-menthyl benzoate, D,L-menthyl isovalerate.

In particular, preference is given to D,L-menthyl benzoate.

The D,L-menthyl derivatives for the inventive process are known per se.

Usually, for the inventive process, lipases from *Candida rugosa* are used.

It is known that lipases can also be produced by recombinant DNA techniques (EP A 238 023). In these the lipase-coding gene is transferred from a selected strain by methods known to those skilled in the art to a receiving organism. This receiving organism produces the lipase.

In a most preferred embodiment, recombinant lipases which are immobilized on a support material are used. Suitable support materials are, for example, plastics such as polypropylene, polystyrene, polyvinyl chloride, polyurethane, polyacrylate, latex, nylon or Teflon, polysaccarides such as agarose or dextran, ion-exchange resins (both cationic and anionic), silicone polymers, for example siloxanes, or silicates, for example glass. Immobilization methods for enzymes are known to those skilled in the art (K. Mosbach, "Immobilized Enzymes", Methods in Enzymology 44, Academic Press, New York, 1976) and comprise cross-linking, adsorption or covalent bonding to the support material.

Lipases from *Candida rugosa* are also commercially marketed, for example lipase AY (distributor: Amano, Nagoya, Japan).

Surprisingly, in a preferred form of the present invention it has been found that hydrolysis of D,L-menthyl benzoate using recombinant lipase from *Candida rugosa* (WO 99/14338) proceeds with very high enantioselectivity (E>100) and an enantiomeric excess of (–)-menthol of >99.9%. This result has been confirmed by gas-chromatographic analysis, NMR spectroscopy and polarimetry.

The differing hydrolytic behavior of the two *Candida rugosa* lipases (commercial and recombinant) can be explained by the fact that commercial preparations can contain not only the desired enzyme, but a great number of isoenzymes having somewhat different properties. SDS-PAGE studies have found that the recombinant lipase used shows only one protein band (see WO 99/14338), while lipase AY shows a plurality of protein bands.

Customarily, the solvent used for the inventive process can be water, aqueous buffer and organic solvents. Organic solvents preferably used are hexane, cyclohexane, heptane, cycloheptane, toluene, dichloromethane, acetonitrile, dimethylformamide, dioxane, tetrahydrofuran or ethanol. The aqueous buffer preferably used is phosphate buffer or acetate buffer.

For the inventive process, generally, 1 to 10000 units (U) are used, preferably 10 to 1000 units (U) of the lipase, based on 0.01 mmol of the menthyl derivative.

The cleavage according to the inventive process is generally carried out in a temperature range from 0 to 90° C., preferably from 20 to 60° C.

The cleavage according to the inventive process is generally carried out in the pH range from 1 to 12, preferably at about pH 7.

The inventive process can be carried out, for example, as follows: In a first step the enzyme is produced in a fermenter in a similar manner to WO 99/14338 (see Example 1). In a second step, the resultant lipase is purified (see Example 1). In a third step the menthyl derivative is enzymatically cleaved (see Example 3).

The pure menthol enantiomers, thus prepared, comply with high analytical and sensory requirements.

EXAMPLES

Example 1

| Fed-batch fermentation Pichia pastoris | |
|---|---|
| Vector: | pGAP (Invitrogen) |
| Plasmid: | Lip 1 (lipase from Candida rugosa) |
| Expression: | constitutive |

Fermentation

The fed-batch fermentation was carried out in a 42 l bioreactor (Bioengineering) at 30° C. and pH 6 in a complex medium. The medium comprised 1% yeast extract, 2% peptone, 1% glycerol and 0.1 M K phosphate buffer pH 6. The feeding solutions, for pure glucose feed, consisted of 20% glucose, for mixed feed, consisted of 20% glucose/5% glycerol. The bioreactor was inoculated with 500 ml of an overnight shake culture having an $OD_{600}$ of 2 to 3 in the above-mentioned medium. The stirrer speed was 400 rpm, aeration rate 15 l(STP)/min. During the fermentation the optical density at 600 nm, the biomass wet matter (BWM), the biomass dry matter (BDM), and the lipolytic activity of the supernatant were determined. The first feed occurred after 24 hours, from then on, every 12 hours, 300 to 600 ml of the feeding solution were fed. The start of the mixed feed was 72 hours. The fermentation was completed after 170 to 190 hours.

The activity, after work-up described below, was 40,000 U/g of freeze-dried concentrate. The total yield was 21 g of dry matter.

Purification of CRL (*Candida rugosa* lipase) Cultured in Complex Medium

Despite secretion of mature *Candida rugosa* lipase in the active form by *Pichia pastoris* into the medium, analysis of the SDS gels prepared found that contaminating proteins were still present in the supernatant. Therefore, a purification protocol was developed for purifying the recombinant lipase.

After cross-flow filtration (Sartorius, Göttingen, Sartocon Cassette: 0.2 μm) 50 ml of the fermentation supernatant were dialyzed (Spectra/Por® dialysis tube) in order to remove the salts interfering with the next purification step. Then, the lipase solution was further concentrated by ultrafiltration using a 30 kD membrane (Pall, Omega Minisette, MW: 30,000). The FPLC column was packed with DEAE-Sepharose, the column was equilibrated with 25 mM tris-HCl buffer (pH 7.5) and the lipase solution was applied. After a wash step using the equilibration buffer, the lipase was eluded using an NaCl gradient. The fractions were tested for lipase activity using the pNPP rapid test (see below). Fractions that had a yellow coloration were combined, ultrafiltered, lyophilized (Finn Aqua Lyovac GT2) and the lypolytic activity determined on a pH stat. The purification protocol is summarized in Table 1.

TABLE 1

Purification table for CRL from culture supernatant of Pichia pastoris in complex medium.

| Volume of lipase solution [ml] | Purification step | Total activity [U]* | spec. activity [U mg$^{-1}$] | Total yield (yield per purification step) [%] |
|---|---|---|---|---|
| 50 | — | 213,500 | 52 | — |
| 270 | Dialysis | 197,100 | 146 | 92 (92) |
| 37 | Ultrafiltration | 185,000 | 166 | 87 (94) |
| 50 | Ion exchange chromatography using DEAE-Sepharose | 89,600 | 5978 | 42 (49) |

*Activities were measured on a pH stat against tributyrin

Enzyme Assay

The activity was routinely determined using a pH stat (Metrohm) and at pH 7.2.

66 mM tributyrin are emulsified with 20 mg/ml of gum arabic stabilizer and homogenized with the Ultraturrax (T25, Janke & Kunkel) for 7 min. at maximum speed.

20 ml of the assay solution were charged and 10 to 100 μl of the enzyme solution were added. The activity was then determined using a pH stat. One unit was defined as the amount of enzyme which releases 1 μmol of fatty acid per minute.

pNPP Rapid Test

To be able to test a large number of samples rapidly, a rapid test is used. Solution A consists of p-nitrophenyl palmitate (pNPP, 10 mm) dissolved in isopropanol. Solution B consists of tris buffer (100 mM, pH 7.5), cholate (0.8% (w/v)) and gum arabic (1% (w/v)). The reaction mixture is composed of 9 parts of solution B and one part of solution A and must always be made up freshly. The solution (50 μl) under test was pipetted into microtitre plates and the reaction mixture (200 μl) was added. The yellow color formed by cleavage of the substrate was estimated either visually or quantified by spectrometry.

Example 2

Preliminary Experiments on Extraction of the Menthyl Benzoate

D,L-Menthyl benzoate was hydrolyzed in sodium phosphate buffer (pH 7.2, 100 mM) containing gum arabic (0.2% (m/v)) as solubilizer. The reaction mixture then needed to be extracted with a suitable solvent for the gas-chromatographic analysis.

To determine a suitable solvent, equimolar amounts of D,L-menthyl benozate and D,L-menthol were dissolved in isooctane in order to obtain a standard for the ratios of the signal areas [menthyl benzoate/menthol]. The gas-chromatographic determination gave a signal area ratio [menthyl benzoate/menthol] of 1.7.

The solvent was then removed on a rotary evaporator, the residue was taken up in 10 ml of sodium phosphate buffer (pH 7.2, 100 mM), gum arabic (0.2% (m/v)) was added, the mixture was homogenized for 10 min and in each case 1 ml aliquots were added to plastic reaction vessels. After incubation for one hour at 40° C., the mixture was covered with a layer of differing solvents (500 μl each) and extracted for 1 hour with shaking. Table 2 shows the signal area ratios [menthyl benzoate/menthol] produced according to GC measurements.

TABLE 2

Solvent for extraction

| Solvent | Signal areas [menthyl benzoate/menthol] |
|---|---|
| Isooctane | 0.2 |
| Hexane | 0.1 |
| Toluene | 1.4 |
| Chloroform | 1.2 |
| Ethyl acetate | 1.7 |
| Diethyl ether | 1.1 |
| Isopropyl ether | 1.4 |

Ethyl acetate was thus, found to be the most suitable solvent for extracting menthyl benzoate and menthol.

Example 3

Hydrolysis of D,L-menthyl Benzoate Using Recombinant Lipase from *Candida rugosa* (Rec. CRL)

The reaction was carried out in each case in 1 ml of sodium phosphate buffer (pH 7.2, 100 mM) at 40° C. using 0.2% (m/v) of gum arabic as solubilizer. The amount of enzyme used was in each case 400 U of purified *Candida rugosa* lipase per 0.01 mmol of D,L-menthyl benzoate. The enantiomeric excesses of menthol were determined by gas chromatography, and those of menthyl benzoate were calculated on the basis of the signal areas.

TABLE 3

Hydrolysis of D,L-menthyl benzoate using rec. CRL.

| Reaction time [h] | Enantiomeric excess [% ee$_S$] | [% ee$_P$] | Conversion rate [%] | Enantio-selectivity |
|---|---|---|---|---|
| Reaction at 40° C. | | | | |
| 2 | 2 | >99 | 2 | >100 |
| 4 | 11 | >99 | 10 | >100 |
| 6 | 28 | >99 | 22 | >100 |
| 8 | 82 | >99 | 45 | >100 |

Table 3 shows that the recombinant lipase from *Candida rugosa* exhibits a very high enantioselectivity (E>100) for the hydrolysis of D,L-menthyl benzoate under the selected reaction conditions.

Example 4

Determination of the Temperature Optimum for Hydrolysis of D,L-menthyl Benzoate

Table 4 summarizes the results of hydrolyzing D,L-menthyl benzoate at different temperatures. The reactions were carried out each in 1 ml of sodium phosphate buffer (pH 7.2, 100 mM) containing 0.2% (m/v) of gum arabic as solubilizer. To determine the temperature optimum, reaction temperatures of 30°, 40°, 50° and 60° C. were chosen. The amount of enzyme used was in each case 800 U of purified *Candida rugosa* lipase per 0.01 mmol of D,L-menthyl benzoate. The enantiomeric excesses of menthol were determined by gas chromatography and those of menthyl benzoate were calculated.

TABLE 4

Hydrolysis of D,L-menthyl benzoate using rec. CRL.

| Reaction time [h] | Enantiomeric excess [% ee$_S$] | [% ee$_P$] | Conversion rate [%] | Enantio-selectivity |
|---|---|---|---|---|
| Reaction at 30° C. | | | | |
| 2 | 19 | >99 | 16 | >100 |
| 4 | 30 | >99 | 23 | >100 |
| 6 | 37 | >99 | 27 | >100 |
| 8 | 42 | >99 | 30 | >100 |
| Reaction at 40° C. | | | | |
| 2 | 22 | >99 | 18 | >100 |
| 4 | 35 | >99 | 26 | >100 |
| 6 | 45 | >99 | 31 | >100 |
| 8 | 84 | >99 | 46 | >100 |
| Reaction at 50° C. | | | | |
| 2 | 63 | >99 | 39 | >100 |
| 4 | 99 | >99 | 50 | >100 |
| Reaction at 60° C. | | | | |
| 2 | 69 | >99 | 41 | >100 |
| 4 | 99 | >99 | 50 | >100 |

Table 4 shows a temperature optimum for hydrolysis of D,L-menthyl benzoate at 50° C. In the case of reaction at 60° C., no further increase in reactivity was observed. At both temperatures, as soon as after 4 hours under the conditions used, a conversion rate of 50% was found and thus complete conversion of the desired menthyl benzoate enantiomer.

Example 5

Comparison Between Recombinant *Candida rugosa* Lipase and Commercially Available Lipases Experiments to date on the hydrolysis of D,L-menthyl benzoate have been carried out using *Candida rugosa* lipase produced using recombinant techniques and purified (Brocca 1998) at the Institute for Industrial Biochemistry, University of Stuttgart.

In addition, the following commercially available lipases have been intensively studied for their stereoselectivity towards racemic menthyl benzoate: commercial lipases from *Candida rugosa* (Amano AY), *Burkholderia cepacia* (formerly *Pseudomonas cepacia*; Roche Diagnostics, Penzberg; Chirazyme L-1), *Rhyzomucor miehei* (Roche Diagnostics, Penzberg; Chirazyme L-9) and *Rhizopus oryzae* (Amano F). Table 5 shows the result of reacting D,L-menthyl benzoate using the lipase from *Rhizomucor miehei* at 40° C. and a reaction time of 16 hours. The enantiomeric excess of product was only 2%, which implies a very low enantioselectivity.

TABLE 5

Hydrolysis of D,L-menthyl benzoate with RML.

| | Enantiomeric excess [% ee$_S$] | [% ee$_P$] | Conversion rate [%] | Enantio-selectivity |
|---|---|---|---|---|
| Rhizomucor miehei lipase | n.d. | 2 | 2 | 2 |

The lipases from *Burkholderia cepacia* and *Rhizopus oryzae* showed no conversion after 16 hours of reaction time.

Table 6 shows the hydrolysis of D,L-menthyl benzoate using the *Candida rugosa* lipase commercially available from Amano Pharmaceutical Co., Ltd., Nagoya Japan. The reactions were carried out at 40° C. and 50° C.

TABLE 6

Hydrolysis of D,L-menthyl benzoate using commercial CRL (Amano AY).

| Reaction time [h] | Enantiomeric excess [% ee$_P$] | Conversion rate [%] | Enantio-selectivity |
|---|---|---|---|
| Reaction at 40° C. | | | |
| 2 | 70 | 20 | 7 |
| 4 | 69 | 65 | |
| 6 | 69 | 78 | |
| 8 | 68 | 91 | |
| Reaction at 50° C. | | | |
| 2 | 69 | 47 | 10 |
| 4 | 59 | 50 | 7 |

Table 6 shows that, although the commercial *Candida rugosa* lipase has a high activity it also has very low enantioselectivity towards menthyl benzoate.

Example 6

Hydrolysis of D,L-menthyl Benzoate Using Recombinant *Candida rugosa* Lipase—Preparative Batch Reaction Equation

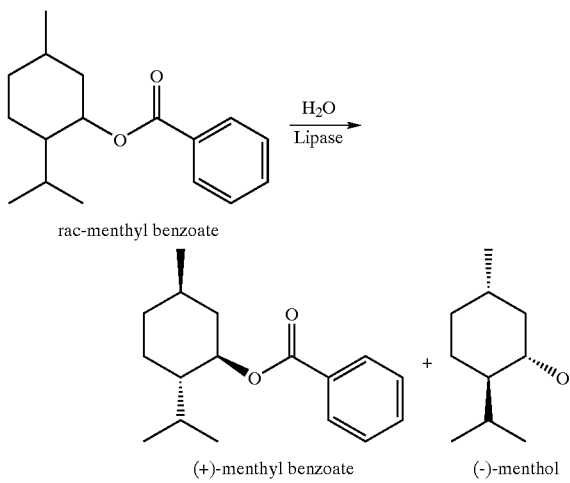

rac-menthyl benzoate (+)-menthyl benzoate    (−)-menthol

Procedure 2.1 g (8 mmol) of D,L-menthyl benzoate were suspended in 250 of sodium phosphate buffer (pH 7.0, 100 mM) in a 500 round-bottom flask and 5 g of recombinant purified *Candida rugosa* lipase were added. The reaction was carried out with vigorous stirring at 40° C. for 20 h. The course of the reaction was followed by thin-layer chromatography. The reaction mixture was then extracted with toluene (250 ml, 2×100 ml), the combined organic phases were dried over $Na_2SO_4$ and concentrated on a rotary evaporator.

The remaining slightly yellowish reaction mixture was purified using column chromatography (silica gel). Petroleum ether/ethyl acetate in a ratio of 10:1 was used as mobile phase.

Yield

A yield of 255 mg (1.6 mMol, 20.0%) of (−)-menthol and 421 mg (1.6 mmol, 20.0%) of menthyl benzoate was obtained.

Characterization

Determination of angle of rotation:

Menthol:

$[\alpha]_D^{20}=-51.3(c=1.00, CH_2Cl_2)[\alpha]_D^{20}=-50 \pm 1$

Menthyl benzoate:

$[\alpha]_D^{20}=+86.3(c=1.00, CH_2Cl_2)[\alpha]_D^{20}=+84.5(c=1.00, CH_2Cl_2)$ NMR Spectroscopy Menthol $^1$H-NMR (CDCl$_3$, 500.1 MHz) δ against TMS: 0.81 (d; J=6.9; 3H); 0.92 (2d; 6 H); 0.97 (d, 1H); 1.10 (d; J=10.2; 1H); 1.40–1.47 (m; 2H); 1.59–1.67 (m; 2H); 1.96 (d, 1H); 2.17 (m; 1H); 3.42 (dt; J=10.4, 4.1; 1H).

$^{13}$C-NMR (CDCl$_3$, 125.8 MHz) δ against TMS: 16.10; 21.03; 22.23; 23.15; 25.83; 31.66; 34.56; 45.06; 50.15; 71.54.

Menthyl Benzoate $^1$H-NMR (CDCl$_3$, 500.1 MHz) δ against TMS: 0.80 (d; J=7.0; 3H); 0.92 (2d; J=5.2, 4.7; 6H); 1.08–1.19 (m; 2H);1.53–1.58 (m; 2H);1.70–1.75 (m; 2H); 1.93–2.00 (m; 1H); 2.11–2.15 (m; 1H); 4.94 (dt; J=10.9, 4.4; 1H); 7.41–7.56 (m; 3H); 8,04 (t; 2H).

$^{13}$C-NMR (CDCl$_3$, 125.8 MHz) δ against TMS: 16.52; 20.78; 22.05; 23.64; 26.50; 31.45; 34.34; 40.98; 47.29; 74.82; 128.29; 129.56; 130.88; 132.68; 166.09.

Gas Chromatography

Menthol: $\geq 99.9\%$ee

Example 7

Hydrolysis of D,L-menthyl acetate

Table 7 summarizes the results of hydrolyzing D,L-menthyl acetate. The reactions were carried out in sodium phosphate buffer (pH 7.2, 100 mM) containing 0.2%(m/v) of gum arabic as solubilizer. To determine the temperature optimum, reaction temperatures of 40°, 50° and 60° C. were selected. The amount of enzyme used was in each case 800 U of purified *Candida rugosa* lipase per 0.01 mmol of D,L-menthyl acetate. The enantiomeric excesses were determined by gas chromatography.

TABLE 7

Hydrolysis of D,L-menthyl acetate using rec. CRL (ITB).

| | Enantiomeric excess | | Conversion rate | Enantio- |
|---|---|---|---|---|
| Reaction time [h] | [% ee$_S$] | [% ee$_P$] | [%] | selectivity |
| Reaction at 40° C. | | | | |
| 2 | 54 | >99 | 35 | >100 |
| 4 | 78 | >99 | 44 | >100 |
| 6 | 89 | >99 | 47 | >100 |
| 8 | 93 | >99 | 48 | >100 |
| Reaction at 50° C. | | | | |
| 2 | 74 | >99 | 43 | >100 |
| 4 | 93 | >99 | 48 | >100 |
| 6 | 98 | >99 | 49 | >100 |
| 8 | 98 | >99 | 50 | >100 |
| Reaction at 60° C. | | | | |
| 2 | 84 | >99 | 46 | >100 |
| 4 | 92 | >99 | 48 | >100 |
| 6 | 96 | >99 | 49 | >100 |
| 8 | 96 | >99 | 49 | >100 |

Table 7 shows that the recombinant lipase from *Candida rugosa* displays high enantioselectivity with respect to hydrolysis of D,L-menthyl acetate under the reaction conditions selected.

For comparison, D,L-menthyl acetate was hydrolyzed using the *Candida rugosa* (Amano AY) commercially available from Amano Pharmaceutical Co., Ltd., Nagoya Japan (Table 8). The table clearly shows that these commercial preparations have significantly lower enantioselectivity than the recombinant *Candida rugosa* lipase towards D,L-menthyl acetate.

TABLE 8

Hydrolysis of D,L-menthyl acetate using commerical CRL (Amano AY).

| | Enantiomeric excess | | Conversion rate | Enantio- |
|---|---|---|---|---|
| Reaction time [h] | [% ee$_S$] | [% ee$_P$] | [%] | selectivity |
| Reaction at 40° C. | | | | |
| 6 | 84 | 48 | 53 | 7 |
| 14 | 76 | 33 | 67 | 4 |

Example 8

Hydrolysis of D,L-menthyl isovalerate

Table 9 summarizes the results of hydrolyzing D,L-menthyl isovalerate. The reactions were carried out in sodium phosphate buffer (pH 7.2, 100 mM) containing 0.2% (m/v) of gum arabic as solubilizer. To determine the temperature optimum, reaction temperatures of 40°, 50° and 60° C. were elected. The amount of enzyme used was in each case 800 U of purified *Candida rugosa* lipase per 0.01 mmol of D,L-menthyl isolvalerate. The enantiomeric excesses were determined by gas chromatography.

TABLE 9

Hydrolysis of D,L-menthyl isovalerate using rec. CRL (ITB).

| Reaction time [h] | Enantiomeric excess [% ee$_S$] | [% ee$_P$] | Conversion rate [%] | Enantio-selectivity |
|---|---|---|---|---|
| Reaction at 40° C. | | | | |
| 2 | 5 | >99 | 5 | >100 |
| 4 | 12 | >99 | 11 | >100 |
| 6 | 22 | >99 | 18 | >100 |
| 8 | 31 | >99 | 24 | >100 |
| Reaction at 50° C. | | | | |
| 2 | 9 | >99 | 8 | >100 |
| 4 | 20 | >99 | 17 | >100 |
| 6 | 40 | >99 | 29 | >100 |
| 8 | 63 | >99 | 39 | >100 |
| Reaction at 60° C. | | | | |
| 2 | 10 | >99 | 9 | >100 |
| 4 | 20 | >99 | 17 | >100 |
| 6 | 30 | >99 | 23 | >100 |
| 8 | 31 | >99 | 24 | >100 |

Table 9 shows that, in the hydrolysis of D,L-menthyl isovalerate using the recombinant *Candida rugosa* lipase, enantiomeric excesses of the product of >99%ee were achieved. The temperature optimum for this reaction was established at 50° C. At 60° C., after 6 hours, a loss in enzyme activity was observed, since the reaction stagnates, which may be due to denaturation of the enzyme at high temperatures.

Example 9

Hydrolysis of D,L-menthyl Anthranilate

D,L-Menthyl anthranilate hydrolysis under the selected standard conditions (sodium phosphate buffer pH 7.2, 100 mM, 30°, 40°, 50° and 60° C., reaction time 24 hours) showed no conversion.

Example 10

Immobilization of the Free Lipase from *Candida rugosa*

Determination of suitable support material.

To immobilize the purified native lipase from *Candida rugosa* various support materials were tested. Immobilization on Celite® 545 (Fluka), EP100 (polypropylene powder 200–400 microns, Akzo Nobel), Hyflo Super Cell® (Fluka), SiO$_2$ (Fluka) and Al$_2$O$_3$ (Fluka) is based on hydrophobic adsorption of the lipase, while bonding to DEAE-Sepharose (Pharmacia Biotech) is due to ionic interactions. Depending on the support material, between 2000 and 3000 units per 1 g of support of purified lipase were used.

After carrying out the immobilization, the samples were filtered and activities in the filtrate and immobilizate were measured on a pH stat (pH 7.2, 30° C.) against tributyrin. Table 10 shows the efficiency of immobilization on the various support materials.

TABLE 10

Activity after immobilization in the filtrate and of the immobilizate.

| Support material | Activity in the filtrate [%] | Activity in the immobilizate [%] |
|---|---|---|
| Celite | 91 | 4 |
| EP100 | 16 | 43 |
| Hyflo | 64 | 8 |
| SiO$_2$ | 48 | 20 |
| Al$_2$O$_3$ | — | — |
| DEAE | 69 | 7 |

Since the highest yields of active, immobilized *Candida rugosa* lipase were achieved using support materials EP100 and SiO$_2$, these immobilizates were used in the hydrolysis of D,L-menthyl benzoate.

Example 11

Hydrolysis of D,L-menthyl benzoate using recombinant *Candida rugosa* lipase immobilized on EP100 and SiO$_2$.

The reaction was carried out in each case in 15 ml of sodium phosphate buffer (pH 7.2, 100 mM) at 50° C. using 0.2% (m/v) of gum arabic as solubilizer. The amount of immobilizate used was in each case 1200 units per 0.1 mmol of D,L-menthyl benzoate. The reaction time was 8 hours. The enantiomeric excesses were determined by gas chromatography.

TABLE 11

Hydrolysis of D,L-menthyl benzoate using immobilized rec. CRL.

| Support material | Enantiomeric excess [% ee$_P$] | Conversion rate [%] | Enantio-selectivity |
|---|---|---|---|
| EP100 | >99 | 43 | >100 |
| SiO$_2$ | >99 | 45 | >100 |

Table 11 shows that the immobilized lipase from *Candida rugosa* exhibits very high enantioselectivity (E>100) with respect to hydrolysis of D,L-menthyl benzoate. This result corresponds to the results obtained using the free lipase from *Candida rugosa*.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing D- or L-menthol or their derivatives in a mixture comprising the step of hydrolyzing D,L-menthyl derivatives enzymatically by lipase in an enantioselective manner in an aqueous medium.

2. A process according to claim 1, wherein said D,L-menthyl derivatives are of the formula:

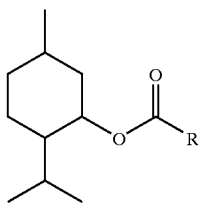

wherein

R denotes hydrogen, unbranched or branched $C_1$–$C_{20}$-alkyl, $C_3$–$C_8$-cycloalkyl, $C_6$–$C_{14}$-aryl, $C_7$–$C_{15}$-arylalkyl, $C_1$–$C_{20}$-alkoxy, $C_1$–$C_{20}$-alkylamino, wherein the above-mentioned hydrocarbon radicals can optionally be monosubstituted or polysubstituted with hydroxyl, formyl, oxy, $C_1$–$C_6$-alkoxy, carboxy, mercapto, sulpho, amino, $C_1$–$C_6$-alkylamino or nitro or halogen.

3. A process according to claim 2, wherein the D,L-menthyl derivatives are aliphatic or aromatic D,L-menthyl esters.

4. A process according to claim 3, wherein the D,L-menthyl derivative is D,L-menthyl benzoate.

5. A process according to claim 1, wherein said lipase is the recombinant lipase LIP1 of *Candida rugosa*.

6. A process according to claim 1, wherein the reaction is carried out in said aqueous medium at about pH 7 and in the temperature range from 10 to 70°C.

7. A process according to claim 1, wherein said lipase is immobilized lipase.

8. A process of preparing D or L-menthol comprising the steps of cleaving D, L-menthyl benzoate enzymatically by *Candida rugosa* lipase in an enantioselective manner and recovering the D or L-menthol from the reaction mixture.

* * * * *